United States Patent [19]

Pohjala et al.

[11] Patent Number: 5,393,748

[45] Date of Patent: Feb. 28, 1995

[54] METHYLENEBISPHOSPHONIC ACID DERIVATIVES

[75] Inventors: Esko Pohjala, Tampere; Marjaana Heikkilä-Hoikka, Vanhalinna; Hannu Nikander, Paattinen; Hannu Hanhijärvi, Turku, all of Finland

[73] Assignee: Leiras Oy, Turku, Finland

[21] Appl. No.: 78,156

[22] PCT Filed: Dec. 18, 1991

[86] PCT No.: PCT/FI91/00395

§ 371 Date: Oct. 20, 1993

§ 102(e) Date: Oct. 20, 1993

[87] PCT Pub. No.: WO92/11269

PCT Pub. Date: Jul. 9, 1992

[30] Foreign Application Priority Data

Dec. 20, 1990 [FI] Finland ................. 906295

[51] Int. Cl.⁶ ................ A61K 31/675; A61K 31/665; C07F 9/02; C07F 9/06
[52] U.S. Cl. ...................... 514/89; 514/86; 514/107; 544/243; 546/21; 558/162
[58] Field of Search ............ 546/21; 514/89, 86, 514/107; 544/243; 558/162

[56] References Cited

U.S. PATENT DOCUMENTS

| | | | |
|---|---|---|---|
| 3,303,139 | 2/1967 | Blaser et al. | 252/180 |
| 3,957,858 | 5/1976 | Kerst | 260/502.4 P |
| 3,962,318 | 6/1976 | Kerst | 260/502.4 P |
| 4,447,256 | 5/1984 | Suzuki et al. | 546/290 |
| 4,870,063 | 9/1989 | Binderup et al. | 514/79 |
| 4,973,576 | 11/1990 | Sakamoto et al. | 514/92 |

FOREIGN PATENT DOCUMENTS

| | | |
|---|---|---|
| 0186405 | 7/1986 | European Pat. Off. |
| 0356866 | 3/1990 | European Pat. Off. |
| 1617118 | 4/1975 | Germany. |

OTHER PUBLICATIONS

Chem. Abstracts, vol. 111, No. 19, 6 (Nov. 1989), p. 748, abstract 174388h and JP,A,63295595 (Yamanouchi Pharmaceutical Co. Dec. 1, 1988).

Chem. Abstracts, vol. 92, No. 7, 18 (Feb. 1980) p. 27, abstract 51765k and Probl. Gematol. Perelir. Kvori, 1979, 24(8), 14–17 (Russ).

Primary Examiner—Cecilia Tsang
Attorney, Agent, or Firm—Wolf, Greenfield & Sacks

[57] ABSTRACT

Novel pharmacologically active methylenebisphosphonates having formula (I) wherein $R^1$–$R^4$ independently are $C_1$–$C_{10}$-alkyl, $C_3$–$C_{10}$-cycloalkyl, aryl, aralkyl, silyl $SiR_3$ or hydrogen, whereby in formula (I) at least one of the groups $R^1$–$R^4$ is hydrogen and at least one of the groups $R^1$–$R^4$ is different from hydrogen, $Q^1$ is hydrogen, hydroxyl, halogen, amino $NH_2$, or $OR'_1$, wherein $R'_1$ is $C_1$–$C_4$-alkyl or acyl, $Q^2$ is the group ($\alpha$) wherein Y is a six-membered heterocyclic group, or a carbocyclic aromatic group, X is a bond, O, S or NR''', wherein R''' is hydrogen, lower alkyl, or acyl, n is the integer 0 to 6, and R' and R'' are hydrogen or lower alkyl provided that as a ring atom of the ring Y and/or a chain atom of the group X, there is always at least one heteroatom from the group O, N and S, including the steroisomers and the salts of the compounds.

5 Claims, No Drawings

METHYLENEBISPHOSPHONIC ACID DERIVATIVES

The invention concerns novel methylenebisphosphonic acid derivatives substituted at the methylene carbon, in particular novel bisphosphonic ester acids and ester salts substituted at the methylene carbon, as well as processes for the preparation of these novel compounds, and pharmaceutical formulations comprising these novel compounds.

Several publications disclose methylenebisphosphonic acids, their salts or some tetraesters, but there are only a few disclosures of corresponding partial esters, tri-, di- and monoesters.

In the patents U.S. Pat. No. 4,447,256 and DE 28 31 578 (Suzuki et al.) a process is disclosed for the preparation of some pyridyl aminomethylenebisphosphonic acid tetraethyl esters. According to the patents the compounds may be used as herbicides, however, no disclosure is found of a pharmaceutical effect of the compounds.

In the patent EP 337 706 (Isomura et al.) the preparation of such cyclyl- or heterocyclyl substituted aminomethylenebisphosphonic acid tetraesters is disclosed, wherein the ring substituent is either partly or fully saturated.

In the patent EP 282 320 (Sakamoto et el.) the preparation of some isoxazolyl substituted aminomethylenebisphosphonic acid tetraalkyl esters as well as the preparation of two partial esters is disclosed.

In the patent EP 298 553 (F. H. Ebetino) the preparation of methylenephosphonoalkyl phosphinates, substituted at the methylene carbon, is disclosed.

The preparation of tetraesters of methylenebisphosphonic acids has been described also in the publications: J. Am. Chem. Soc. 78, (1956) 4450; J. Chem. Soc. (1959) 2272; J. Am. Chem. Soc. 84 (1962) 1876; J. Org. Chem. 35, (1970) 3149; J. Org. Chem. 36, (1971) 3843 and Phosphorus, Sulfur and Silicon 42, (1989) 73, EP patent application 221 611.

According to the invention it has been discovered that the novel substituted partial esters of methylenebisphosphonic acids and their salts in many cases exhibit more favourable properties than the corresponding bisphosphonic acids and salts due to their better kinetics and availability, their ability to participate as complex formers in the regulation of the metabolism of the organism being maintained.

They are well suited for the treatment of disorders relating to the metabolism of calcium and of other, especially bivalent metals. They may be used both for the treatment of diseases in the skeletal system, especially of bone formation and resorption disorders, such as of osteoporosis and Paget's disease, as well as for the treatment of diseases in the soft tissues, such as of deposition and mineralisation conditions and bone formation disorders.

On the other hand, being pyrophosphate analogs, the new substituted methylenebisphosphonic acid derivatives also are suitable for the treatment of disorders in the (pyro)phosphate functions of the organism, including those functions, wherein an active, but disturbance-prone or wrongly functioning organic part is coupled to (pyro)phosphate or acts as a metal complex or a combination of the last mentioned.

The novel bisphosphonates regulate either directly or over an indirect mechanism the quality and level of cations and/or pyrophosphate compounds freely present in the body fluids as well as of that binding to, active in and liberated from the tissues. Thus they are able to regulate the cellular metabolism, growth and destruction. Consequently they are useful for the treatment of e.g. cancer of the bone and metastases thereof, ectopic calcifications, urolithiasis, rheumatoid arthritis, bone infections and bone degradation.

Typical for the novel substituted methylenebisphosphonates is a selective desired and controlled action, providing for a better therapeutic index.

The invention concerns novel methylenebisphosphonic acid derivatives of the general formula I

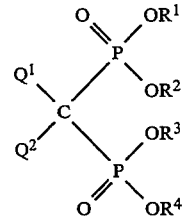

in which formula $R^1$, $R^2$, $R^3$ and $R^4$ independently are a straight or branched optionally unsaturated $C_1$-$C_{10}$-alkyl, optionally unsaturated $C_3$-$C_{10}$-cycloalkyl, aryl, aralkyl, silyl $SiR_3$ or hydrogen, whereby in the formula I at least one of the groups $R^1$, $R^2$, $R^3$ and $R^4$ is hydrogen and at least one of the groups $R^1$, $R^2$, $R^3$ and $R^4$ is different from hydrogen, $Q^1$ is hydrogen, hydroxyl, halogen, amino $NH_2$, or $OR'_1$, wherein $R'_1$ is $C_1$-$C_4$-alkyl or acyl, $Q^2$ is the group

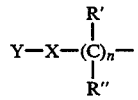

wherein Y is an optionally substituted, saturated, partly saturated or aromatic six-membered heterocyclic group, or a carbocyclic aromatic group, whereby the heterocyclic groups can contain 1 to 3 heteroatoms from the group N, O and S, X is a bond, O, S or NR''', wherein R''' is hydrogen or lower alkyl with 1 to 4 C-atoms, acyl, n is the integer 0 to 6, and R' and R'' are independently hydrogen or lower alkyl with 1 to 4 C-atoms, provided that as a ring atom of the ring Y and/or a chain atom of the group X, there is always at least one heteroatom from the group of O, N and S, including the stereoisomers, such as the geometrical isomers and the optically active isomers, of the compounds, as well as the pharmacologically acceptable salts of the compounds.

The groups $R^1$, $R^2$, $R^3$ and $R^4$ are independently a straight or branched alkyl, alkenyl or alkynyl group and they contain 1 to 10, respectively 2 to 10 carbon atoms, preferably 1 to 7, respectively 2 to 7, and advantageously 1 to 4, respectively 2 to 4 carbon atoms.

Optionally unsaturated cycloalkyl is cycloalkyl or cycloalkenyl with 3 to 10 C-atoms, preferably, however, cyclopropyl, -butyl, -pentyl, or -hexyl.

Aryl or aralkyl as the groups $R^1$, $R^2$, $R^3$ and $R^4$ means optionally $C_1$-$C_4$-lower alkyl, -lower alkoxy or halogen substituted monocyclic aryl or aralkyl, such as phenyl and benzyl, preferably, however, unsubstituted phenyl or benzyl.

Halogen is fluorine, chlorine, bromine or iodine.

Acyl is alkyl-, aryl- or arylalkylcarbonyl, or alkoxy-, aryloxy- or aralkoxycarbonyl, wherein alkyl contains 1 to 4 carbon atoms, and aryl and aralkyl have the same meaning as before.

In the silyl group $SiR_3$ the group R is lower alkyl containing 1 to 4 C-atoms, and is especially methyl, ethyl, isopropyl, butyl, t-butyl, or it is phenyl or R-substituted phenyl, whereby also different combinations of lower alkyl and phenyl groups come into question, such as dimethyl t-butyl, methyl diisopropyl, dimethyl phenyl, diethyl phenyl, methyl t-butyl phenyl, diisopropyl-(2,6-dimethyl phenyl).

As the heteroaromatic and saturated heterocyclic group Y, respectively, nitrogen, oxygen and/or sulfur containing six-membered unsaturated ring groups come into question, such as pyridine, pyrimidine, pyrazine, pyridazine, oxazine, thiazine, triazine, as well as corresponding saturated groups, such as piperidine, piperazine, morpholine, oxathiane, dithiane, thiomorpholine etc. The hetercyclic groups may be substituted as has been described for aryl and aralkyl below.

The group Y means as a carbocyclic aromatic group a substituted or unsubstituted aromatic ring, such as a monocyclic aryl or aralkyl, especially phenyl, or a conjugated or bridged unsaturated or partly saturated ring system, such as naphtyl, phenanthryl, indenyl, indanyl, tetrahydronaphtyl, biphenyl, di- and triphenyl methyl etc.

Monocyclic aryl and aralkyl may be illustrated with the formula

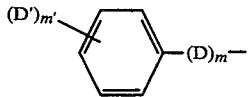

wherein the groups D′ mean independently $C_1$–$C_4$-alkyl, -alkoxy, halogen or nitro, m′ is the integer 0 to 3 and m the integer 0 or 1, and D means a straight or branched $C_1$–$C_6$-alkylene, -alkenylene or -alkynylene. Halogen is chlorine, bromine, fluorine or iodine.

The group Y—X— in the formula I contains at least one heteroatom from the group O, N and S as a ring atom in Y and/or as chain atom in X.

Salts of the compounds of the formula I are especially their salts with pharmaceutically acceptable bases, such as metal salts, for example alkalimetal salts, especially lithium, sodium and potassium salts, alkaline earth metal salts, such as calcium or magnesium salts, copper, aluminium or zinc salts, as well as ammonium salts with ammonia or with primary, secondary and tertiary, both aliphatic and alicyclic as well as aromatic amines, and quaternary ammonium salts, such as halides, sulphates and hydroxides, salts with aminoalcohols, such as ethanol-, diethanol- and triethanolamines, tris(hydroxymethyl)aminomethane, 1- and 2-methyl- and 1,1-, 1,2- and 2,2-dimethylaminoethanols, N-mono- and N,N-dialkylaminoethanols, N-(hydroxymethyl- and ethyl)-N,N-ethanediamines, as well as amino crown ethers and cryptates, and heterocyclic ammonium salts, such as azetidinium, pyrrolidinium, piperidinium, piperazinium, morpholinium, pyrrolium, imidazolium, pyridinium, pyrimidinium, quinolinium, etc., salts.

Good results have been obtained with the following mono- or dimethyl-, mono- or diethyl-, mono- or diisopropyl esters, wherein $Q^1$ is hydrogen and Y is a heterocyclic group, such as unsubstituted or methyl substituted pyridine or piperidine, n is 0, and X is NH or S, and especially good results have been obtained with the following compounds:

[[(6-methyl-2-pyridinyl)amino]methylidene]bisphosphonic acid P,P′-diethyl ester,

[[(2-pyridinyl)amino]methylidene]bisphosphonic acid P,P′-diethyl ester,

[[(2-pyridinyl)amino]methylidene]bisphosphonic acid P,P-methyl ester,

[[(3-methyl-2-pyridinyl)amino]methylidene]bisphosphonic acid P,P′-diethyl ester,

[[(4-methyl-2-pyridinyl)amino]methylidene]bisphosphonic acid P,P′-diethyl ester,

[[(2-pyridinyl)thio]methylidene]bisphosphonic acid monoisopropyl ester,

[[(4-chlorophenyl)thio]methylidene]bisphosphonic acid P,P′-dimethyl and monoethyl ester,

[[(6-methyl-2-pyridinyl)amino]methylidene]bisphosphonic acid monoethyl ester,

[[(3-methyl-2-pyridinyl)amino]methylidene]bisphosphonic acid monomethyl ester,

[[1-hydroxy-2-(3-pyridinyl)]ethylidene]bisphosphonic acid monoisopropyl ester,

[[1-hydroxy-2-(3-pyridinyl)-]ethylidene]bisphosphonic acid monomethyl ester,

[2-(2-pyridinyl)ethylidene]bisphosphonic acid monoisopropyl ester,

[2-(3-pyridinyl)ethylidene]bisphosphonic acid monomethyl ester,

[[(3-pyridinyl)amino]methylidene]bisphosphonic acid P,P′-dimethyl ester,

[[(3-pyridinyl)thio]methylidene]bisphosphonic acid P,P′-diethyl ester,

[[(4-pyridinyl)thio]methylidene]bisphosphonic acid P,P′-diethyl ester,

[[(3-pyridinyl)thio]methylidene]bisphosphonic acid monoisopropyl ester.

The invention concerns also a process for the preparation of the compounds of the formula I, according to which a) a methylenebisphosphonic acid tetraester of the formula II

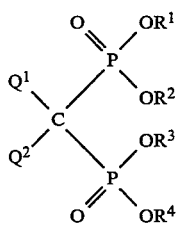

in which formula $Q^1$ and $Q^2$ have the same meaning as above, and $R^1$, $R^2$, $R^3$ and $R^4$ have the same meaning as above, except hydrogen, is selectively hydrolysed to a triester corresponding to the formula I, wherein one of the groups $R^1$, $R^2$, $R^3$ and $R^4$ has the meaning of hydrogen, or a salt thereof, or to a diester corresponding to the formula I, wherein two of the groups $R^1$, $R^2$, $R^3$ and $R^4$ have the meaning of hydrogen, or a salt thereof, or to a monoester corresponding to the formula I, wherein three of the groups $R^1$, $R^2$, $R^3$ and $R^4$ have the meaning of hydrogen, or a salt thereof, or b) a bisphosphonic acid of the formula

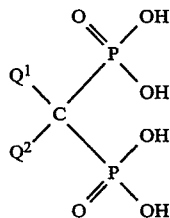

VII or a metal or ammonium salt of this compound, or the corresponding acid tetrachloride, wherein $Q^1$ and $Q^2$ have the same meaning as above, is esterified selectively by reacting the same with an esterification reagent corresponding to the desired groups $R^1$, $R^2$, $R^3$ and $R^4$, to a monoester corresponding to the formula I, wherein three of the groups $R^1$, $R^2$, $R^3$ and $R^4$ have the meaning of hydrogen, or to a diester corresponding to the formula I, wherein two of the groups $R^1$, $R^2$, $R^3$ and $R^4$ have the meaning of hydrogen, or to a triester corresponding to the formula I, wherein one of the groups $R^1$, $R^2$, $R^3$ and $R^4$ has the meaning of hydrogen, or to the corresponding ester salts of the said partial esters, or c) a phosphonate having the formula

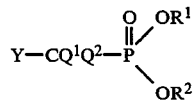

IX is reacted with an activated phosphate or a hydrogen phosphonate corresponding to the formula X

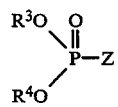

X wherein in the formulas Y is hydrogen, hydroxy or halogen or other leaving group, Z is hydrogen, halogen, acyloxy, sulphonyloxy, alkoxy or aryloxy, and $R^1$, $R^2$, $R^3$ and $R^4$ and $Q^1$ and $Q^2$ have the same meaning as in the formula I, or $Q^1$ and $Q^2$ form a double-bonded oxygen or an imino group, or is reacted with a phosphite corresponding to the formula X, or d) a bisphosphonate corresponding to the formula I, which instead of $Q^2$ has a carbanion site, is reacted with ω-leaving group substituted $Q^2$, or a bisphosphonate corresponding to the formula I, which instead of $Q^2$ contains a leaving group, is reacted with a ω-carbanion corresponding to $Q^2$, or a ($Q^2$-$C_1$)-ω-carbanion is added by Michael addition in alkylidenebisphosphonates, or e) a bisphosphonite compound having the formula

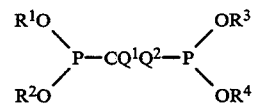

wherein $R^1$, $R^2$, $R^3$ and $R^4$ and $Q^1$ and $Q^2$ have the same meaning as in the formula I, or the corresponding hydrogen phosphonate compound, is oxidized to a compound of the formula I, and if desired, the partial ester acids obtained according to steps a) to e) are converted to partial ester salts, or the partial ester salts obtained are converted to the partial ester acids, and/or, if desired, a compound obtained according to the formula I is converted into some other compound according to the formula I by hydrolyzing, esterification or transesterification, and/or in a compound of the formula I, a group $Q^1$ is converted into another group $Q^1$ within the scope of the definition.

According to one process the compounds are thus prepared by selective hydrolysis of the tetraesters corresponding to the formula I. As the starting material thus a tetraester is used, wherein the groups $R^1$ to $R^4$ and $Q^1$ and $Q^2$ have the same meaning as above and this tetraester is hydrolyzed stepwise to the triester III, diester IV and V and the monoester VI. If necessary, the partial ester or its salt may be isolated and purified by extraction, fractional crystallization or chromatographically, and if desired, a free acid may be converted into a salt or a salt into the free acid.

This reaction is shown in the appended Scheme 1 (the reaction takes place in the direction of the upper arrow).

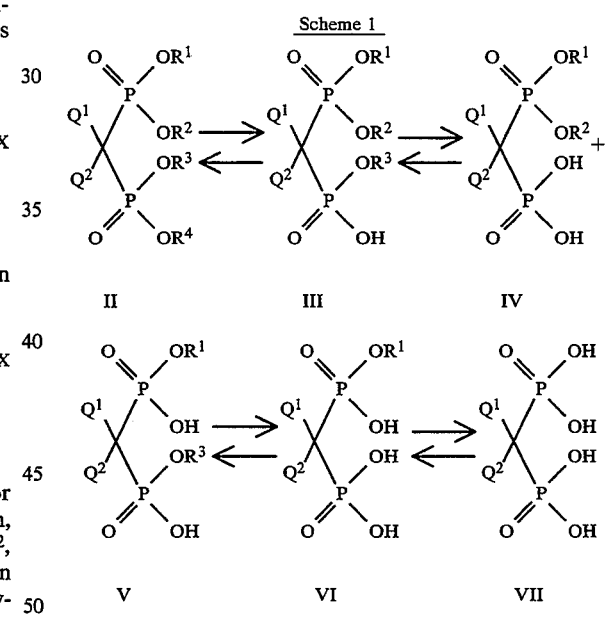

Scheme 1

The hydrolysis of the tetraesters II may be carried out by treating both with an acid and a base, using thermal cleaving, and in certain cases also using water, alcohols, or other neutral or non-neutral transalkylation, -silylation and -arylation reagents. The hydrolysis takes place advantageously at a temperature range of 10° to 150 ° C. The acids are advantageously conventional inorganic acids, such as hydrochloric acid, sulphuric acid, phosphoric acid, and Lewis acids, such as borotrifluoride etherate, titanium tetrachloride, etc., as well as a number of organic acids, such as oxalic acid, formic acid, acetic acid and other carboxylic acids, methanesulphonic acid and other sulphonic acids, such as tosyl acid, further chlorine and fluorine substituted carboxylic and sulphonic acids, such as trichloroacetic acid and trifluoromethanesulphonic acid, and their aqueous solutions.

The bases are advantageously alkali and ammonium hydroxides and ammonia and the aqueous solutions thereof, as well as a number of amines, such as primary, secondary and tertiary amines, such as e.g. diethyl-, triethyl-, diisopropyl- and tributylamine, aniline, N- and N,N-alkyl substituted anilines and heterocyclic amines, such as pyridine, morpholine, piperidine, piperazine etc., and hydrazines, such as N,N-dimethyl hydrazine.

In addition, acids and bases bound to a solid substrate may be used, such as Amberlites, either in the presence of an organic solvent or water or various solvent mixtures, or in the absence thereof.

Further by treating with certain alkalimetals, such as sodium and litium, or with suitable inorganic salts, such as with sodium iodide, litium bromide, ammonium chloride and NaBr/PTC, the ester group may be converted to its corresponding salt, such as to the sodium, ammonium and litium salt.

Thermal cleaving usually takes place at a temperature of about 100° to 400° C., usually, however, at a temperature of not more than 250° C. The presence of a suitable catalyst, such as an acid or an acid solution, or a quaternary ammonium salt, makes it possible to perform the reaction faster and at a lower temperature. Certain active substituents, such as benzyl and allyl, may be removed by catalytic reduction or electrolytically.

To improve solubility and to control the reaction temperature during the reactions, organic, inert solvents, such as hydrocarbons, lower alcohols and stable ketones and esters, alkyl halides, such as chloroform, dichloromethane and -ethane, ethers, such as dioxan, dimethoxy ethane, diglyme, acetonitrile, etc., may be used as co-solvents.

When the groups $R^1$ to $R^4$ in the tetraester according to the formula II are the same, the hydrolysis takes place stepwise, and it is interrupted when the concentration of the desired partial ester is at its greatest.

In order to prepare a specific partial ester structure, it is advantageous to use a tetraester of the formula II wherein the ester groups are not the same, but groups which are different with respect to the hydrolysis rate. It has, for example, been discovered that the hydrolysis rate of alkyl and silyl esters is dependant on the structure as follows:

silyl > tert > sec > prim

It is possible to affect the hydrolysis rate by changing also the size and shape of the alkyl and silyl substituent as well as by electronical factors. It is often possible to perform a transesterification in order to change the stepwise hydrolysis of the different ester sites. Especially the methyl ester may advantagenously be converted to the corresponding acid over a silyl ester.

Pure partial esters may thus be prepared in an advantageous manner by performing a selective hydrolysis of mixed esters of the formula I, which have been prepared using ester groups which are advantageous from the point of view of hydrolysis.

Also other selective hydrolysis reactions known especially from phosphate and monophosphonate chemistry may be used.

The progress of the hydrolysis may be followed for example chromatographically or by means of $^{31}$P-NMR spectroscopy. The reaction may be interrupted when the level of the desired partial ester is at its greatest and the product may be isolated from the reaction mixture either as the free acid or as a salt by precipitation, extraction or chromatographically, and the salt form may be converted to the free acid or the free acid to its salt.

The compounds according to this invention may be prepared also by selective esterification of bisphosphonic acids in accordance with the above mentioned reaction Scheme 1 (the reaction takes place in the direction of the lower arrow).

As a starting material a tetraacid according to the formula VII ($R^1$ to $R^4$=H) may then be used, which can be as a free acid or in the form of a salt, such as a metal or ammonium salt, or the corresponding phosphonic acid tetrachloride may be used, and depending on the desired end result, 1 to 4 equivalents of the desired aliphatic or aromatic alcohol, or the corresponding activated alkylation, silylation and arylation reagents, such as ortoesters, ketene acetals and other suitable transfer reagents for alkyl, silyl and aryl groups, such as diazo compounds, active carboxylic acid esters, sulphates, etc. The reaction is usually performed under anhydrous conditions, preferably in the temperature range of 0° to 150° C., or when using an inert co-solvent, at the boiling point thereof.

The esters II to IV may also be prepared in a nucleophilic substitution reaction between the bisphosphonate anion, often the ammonium salt, and an organic halide or sulphonate, or in a condensation reaction between a phosphonic acid group and a suitable alcohol or a phenol using a reagent for cleaving off water, such as carbodiimides.

Pure partial esters, also mixed esters, may thus be prepared by selective esterification, if necessary stepwise, of tetraacids of the formula VII. Also other selective esterification reactions may be applied known primarily from phosphate and monophosphonate chemistry.

The progress of the esterification reactions may be followed, for example, chromatographically or using $^{31}$P-NMR and the reaction is interrupted when the content of the desired partial ester is at its greatest and this is isolated from the reaction mixture by precipitation, extraction or chromatographically and, if desired, a salt form obtained is converted to the free acid or the free acid is converted to its salt.

Partial esters according to .the invention may also be prepared by constructing the P—C—P frame from its parts

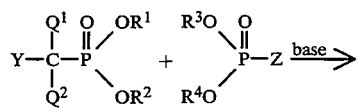

wherein in the formula Y is hydrogen, hydroxy or halogen or other leaving group, Z is halogen, acyloxy, sulphonyloxy, alkoxy, or aryloxy, and $R^1$ to $R^4$ and $Q^1$ and $Q^2$ have the meaning given above, or $Q^1$ and $Q^2$ are double-bonded oxygen or an imino group. As the base, for example, sodium hydride, butyl litium or litium diisopropylamide may be used. In the starting material optionally present free acid sites (one of the groups $R^1$ to $R^4$=H) have to be neutralized, by using a sufficient amount of base, prior to the coupling reaction. Also active sites in the groups $Q^1$ and $Q^2$ have to be neutralized or the said active site has to be protected with a protecting group.

Also the Michaelis-Arbuzov reaction may be used, whereby the second reacting compound is a phosphite, or the Michaelis-Becker reaction, whereby Z is hydrogen.

In certain instances the group Q¹ may be introduced by an exchange reaction, or an oxidation or reduction reaction, for example hydroxyl may be obtained from hydrogen, halogen or amino, the amino group may be obtained from halogen or hydroxyl, and hydrogen may be obtained from halogen, and halogen may be obtained from hydrogen.

Q² may also be brought into the molecule either by a reaction involving a bisphosphonate carbanion or corresponding C-halogen or other leaving group, whereby the Q²-reagent is ω-substituted with a leaving group, or correspondingly is a ω-carbanion.

The compounds according to the invention may also be prepared by applying the Michael addition to alkylidene phosphonates described in the EP patent application 0 221 611.

The esters according to the invention may also be prepared from P—C—P-structures at a lower oxidation level by oxidation

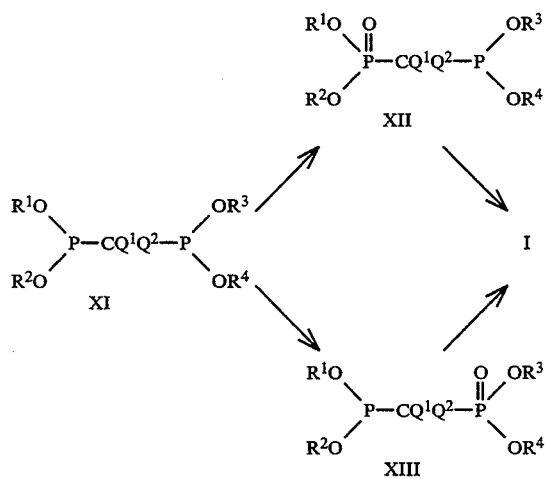

whereby in the formulas R¹ to R⁴ and Q¹ and Q² have the meaning given above, and whereby the phosphonite structure may exist in an equilibrium with the hydrogenphosphonate structure. All conventional oxidation agents, or their solutions, such as hydrogen peroxide, perhalogen compounds, peracids, permanganate etc., come into question.

The partial esters of bisphosphonic acid according to the invention may also be prepared from other partial esters by performing an intra- or intermolecular exchange reaction.

The tetraesters II and corresponding tetraacids IV used as starting materials in the above reactions may be prepared by processes known as such from literature by constructing the P—C—P frame from its parts, for example using the above mentioned Michaelis-Becker-, Michaelis-Arbuzov- or carbanion reaction, also stepwise, whereby R¹ to R⁴ may be chosen and advantageously introduced as parts of the bisphosphonate taking into account the structure of the desired partial ester, and by suitably substituting this frame or an anion obtained therefrom, for example by an alkylation or an addition reaction.

N-substituted (aminomethylidene)bisphosphonic acid tetraesters may be prepared by reacting an amino substituted compound with alkyl ortoformiate and reacting the imino ether derivative obtained as an intermediate with dialkyl phosphite either as such or in purified form.

N-substituted (aminoalkylidene)bisphosphonic acid esters may also be prepared for example in a reaction between alkenyl bisphosphonic acid esters and amino derivates, or by substituting suitably (alkylidene)bisphosphonic acid esters.

O-substituted (oxyalkylidene)bisphosphonic acid tetraesters may be prepared for example by reacting suitable dichloroalkyl ethers with trialkyl phosphites and by reacting the thus obtained dialkyl (chloroalkoxymethyl)phosphonates with sodium dialkyl phosphite.

(Thiomethylidene)bisphosphonates may suitably be prepared by reacting a disulfide and a methylenebisphosphonate anion.

Taking into account the preparation of a desired partial ester, the prepared tetraesters may, if necessary, be converted to other suitable tetraesters using exchange reactions. Thereby the groups OR¹ to OR⁴ may be exchanged directly or over the corresponding phosphonochloride or by applying other known processes.

Optically active partial esters may be best prepared by using known optically active compounds, such as optically active alcohols, in the preparation of the above mentioned starting materials, intermediates and end products, or in the exchange reactions.

The properties of the compounds according to the invention have been tested in the following test systems.

The parathyroid hormone stimulated bone resorption inhibition activity of the compounds in vitro in mouse calvaria, as well as the inhibition of retinoid induced bone resorption in thyroparathyroidectomised rats in vivo were determined (Reynolds & Dingle (Calc Tiss Res 1970; 4:339, and Trechsel et al. (J Clin Invest 1987; 80:1679)).

TABLE 2

| Antiresorptive activity Inhibition of resorption (%) | | |
|---|---|---|
| | 100 μm in vitro | 150 μmole/kg in vivo |
| Clodronate | 43 | 64 |
| [[(3-methyl 2-pyridinyl)amino] methylidene]bisphosphonate | 51 | ND |
| [[(2-pyridinyl)amino]- methylidene]bisphosphonate | 56 | >100 |
| P,P'-diethyl [[(3-methyl 2-pyridinyl)amino]- methylidene]bisphosphonate | 43 | 66 |
| P,P'-diethyl [[(2-pyridinyl)amino]- methylidene]bisphosphonate | 33 | 65 |
| monoisopropyl [[(2-pyridinyl)thio]- methylidene]bisphosphonate | 50 | 87 |

ND = Not determined.

From the table the superiority of the compounds of the invention, especially their better relative in vivo-anti-resorptive activity is apparent when taking into account that they do not bind to hydroxy apatite, even though they inhibit crystal growth. They provide for a better therapeutic index, exhibiting lesser side effects.

The partial esters of substituted bisphosphonic acids of the formula I may be used as pharmaceuticals as such, or as their pharmacologically suitable salts, such as the alkali or ammonium salts. Such salts may be prepared by reacting the ester acids with the corresponding inorganic or organic bases. Depending on the reaction conditions, the ester salts may be formed also directly in the above mentioned reactions.

The new compounds I according to this invention may be administered enterally or parenterally. All conventional administration forms, such as tablets, capsules, granules, syrups, solutions, implants and suspensions come into question. Also all adjuvants for manufacture, dissolution and administration of the preparation, as well as stabilizers, viscosity regulating and dispersion agents and buffers, may be used.

Such adjuvants include i.a. tartrate and citrate buffers, alcohols, EDTA and other nontoxic complexing agents, solid and liquid polymers and other sterile substrates, starch, lactose, mannite, methylcellulose, talc, silicic acids, fatty acids, gelatine, agar-agar, calcium phosphate, magnesium stearate, animal and vegetable fats and, if desired, flavouring and sweetening agents. The dosage depends on several factors, for example on the manner of administration, species, age and individual condition. The daily doses are about 0.1 to 1000 mg, usually 1 to 100 mg per person, and they may be administered as a single dose or may be divided into several doses. In the following, examples of a typical capsule and a tablet are given:

|  | mg/caps. |
|---|---|
| Capsule | |
| Active ingredient | 10.0 mg |
| Starch | 20.0 mg |
| Magnesium stearate | 1.0 mg |
| Tablet | |
| Active ingredient | 40.0 mg |
| Microcrystalline cellulose | 20.0 mg |
| Lactose | 67.0 mg |
| Starch | 10.0 mg |
| Talc | 4.0 mg |
| Magnesium stearate | 1.0 mg |

For medicinal use, also an intramuscularly or parenterally administered preparation may be made, for example an infusion concentrate, wherein as adjuvants e.g. sterile water, phosphate buffer, NaCl, NaOH or HCl or other known pharmaceutical adjuvants suitable for the purpose may be used.

The compounds in ester-acid form according to the invention are liquids or waxy substances, usually soluble in organic solvents and in some instances in water. The ester salts are solid, crystalline or typically powdery substances which usually dissolve well in water, in some instances in organic solvents, but only certain structure types being poorly soluble in all solvents. The compounds are very stable, also in their neutral solutions at room temperature.

The structure of the compounds may easily be verified with $^1$H-, $^{13}$C- and $^{31}$P-NMR-spectroscopy and FAB-masspectrometry, or when silylated, with EI-masspectrometry. For concentration and impurity determinations 31P-NMR-spectroscopy is very suitable (85% $H_3PO_4$ $\delta=0$). Also for polar compounds as such ion exchange and exclusion-HPLC may be used and for tetraesters and silylated ester acid derivatives GLC or GC/MS may be used. From the compounds sodium and other metals were determined separately as well as the possible crystal water content. From the amine salts, nitrogen was determined.

The following examples illustrate the invention without limiting the same in any way.

PREPARATION OF STARTING MATERIALS

Example A

Preparation of [[(3-Methyl-2-pyridinyl)amino]methylidene]bisphosphonic Acid Tetraethyl Ester A mixture of 2-amino-3-methylpyridine (0.2 moles), triethyl ortoformiate (0.24 moles) and diethylphosphite (0.42 moles) was heated at 150° C. for 30 minutes, whereafter the ethanol formed in the reaction was distilled off. The mixture was cooled and the raw product was purified chromatographically (eluent methanol-dichloromethane, 1:1). Yield 37 g (49%; 31-P NMR 18.86 ppm; $CDCl_3$).

In the same manner may be prepared:

[[(4-Methyl-2-pyridinyl)amino]methylidene]bisphosphonic acid tetraethyl ester from 2-amino-4-methylpyridine (31-P NMR 18.60 ppm; $CDCl_3$).

[[(6-Methyl-2-pyridinyl)amino]methylidene]bisphosphonic acid tetraethyl ester from 2-amino-6-methylpyridine (31-P NMR 18.75 ppm; $CDCl_3$).

[[(2-Pyridinyl)amino]methylidene]bisphosphonic acid tetraethyl ester from 2-aminopyridine (31-P NMR 18.62 ppm; $CDCl_3$).

[[(3-Pyridinyl)amino]methylidene]bisphosphonic acid tetraethyl ester from 3-aminopyridine.

[[(3-Pyridinyl)amino]methylidene]bisphosphonic acid tetraisopropyl ester from 3-aminopyridine.

[[(2-Pyridinyl)amino]methylidene]bisphosphonic acid tetramethyl ester from 2-aminopyridine (31-P NMR 16.00 ppm; $CDCl_3$).

[[(4-Pyridinyl)amino]methylidene]bisphosphonic acid tetraethyl ester from 4-aminopyridine.

[[(3-Hydroxy-2-pyridinyl)amino]methylidene]bisphosphonic acid tetraethyl ester (31-P NMR 18.76 ppm; $CDCl_3$).

[[(4-Methoxy-3-pyridinyl)amino]methylidene]bisphosphonic acid tetraethyl ester (31-P NMR 18.15 ppm; $CDCl_3$).

[[(4,6-Dihydroxy-2-pyrimidyl)amino]methylidene]bisphosphonic acid tetraethyl ester.

Example B

Preparation of [1-Hydroxy-2-(2-pyridinyl)ethylidene]bisphosphonic Acid Tetramethyl Ester To a chloroform solution of trimethylphosphite (0.1 moles) and dimethyl phosphite (0.1 moles) (2-pyridinyl) acetyl chloride (0.1 moles) dissolved in chloroform was slowly added at 0° C. The mixture was heated at 80° C. for 10 hours. The solvent was evaporated at reduced pressure, and the product purified with flash chromatography (eluent methylene chloride-methanol 1:1). Yield 14 g (41%).

In the same manner may be prepared:

[1-Hydroxy-2-(3-pyridinyl)ethylidene]bisphosphonic acid tetraisopropyl ester (31-P NMR 20.02 ppm; $CDCl_3$).

[1-Hydroxy-2-(4-pyridinyl)ethylidene]bisphosphonic acid tetraisopropyl ester.

Example C

**Preparation of
[2-(2-Pyridinyl)ethylidene]bisphosphonic Acid
Tetraisopropyl Ester**

Sodium hydride (0.15 moles) was slurried in a nitrogen atmosphere into dry toluene and tetraisopropyl methylenephosphonate (0.065 moles) was added slowly. The solution was stirred until the generation of hydrogen had ceased. 2-picolyl chloride (0.72 moles) dissolved in dimethylformamide was added slowly and the solution refluxed for 12 hours. The solvents were evaporated and the product purified with flash chromatography (eluent toluene-acetone, 1:1). Yield 58%, In the same manner may be prepared:

[[(2-Pyridinyl)thio]methylidene]bisphosphonic acid tetramethyl ester from 2,2'-dipyridinyl disulphide (31 P-NMR 23.26 ppm; $CDCl_3$).

[[(2-Pyridinyl)thio]methylidene]bisphosphonic acid tetraisopropyl ester from 2,2'-dipyridinyl disulphide (31-P NMR 18.85 ppm; $CDCl_3$).

[2-(3-pyridinyl)ethylidene]bisphosphonic acid tetraisopropyl ester (31-P NMR 20.13 ppm; $CDCl_3$).

[2-(3-pyridinyl) ethylidene]bisphosphonic acid tetraethyl ester (31-P NMR 22.00 ppm; $CDCl_3$).

[[(3-Pyridinyl)thio]methylidene]bisphosphonic acid tetraisopropyl ester from 3,3'-dipyridinyl disulphide.

[[(4-Pyridinyl)thio]methylidene]bisphosphonic acid tetraethyl ester from 4,4'-dipyridinyl disulphide.

[[(2-Pyridinyl)thio]methylidene]bisphosphonic acid tetraethyl ester from 2,2'-dipyridinyl disulphide

[[(2-Pyridinyl)thio]methylidene]bisphosphonic acid isopropyl trimethyl ester from 2,2'-dipyridinyl disulphide and isopropyl trimethyl methylenebisphosphonate (31-P NMR 20.21/17.5 ppm; $CDCl_3$).

[[(4-Chlorophenyl)thio]methylidene]bisphosphonic acid tetraisopropyl ester from bis(4-chlorophenyl) disulphide (31-P NMR 18.14 ppm; $CDCl_3$).

[[(4-Chlorophenyl)thio]methylidene]bisphosphonic acid tetraethyl ester from bis(4-chlorophenyl) disulphide

[2-(2-Pyridinyl)ethylidene)bisphosphonic acid P,P-dimethyl P',P'-diisopropyl ester from 2-picolyl chloride and P,P-dimethyl P',P'-diisopropyl methylenebisphosphonate.

[2-(3-Pyridinyl)ethylidene]bisphosphonic acid P,P'-dimethyl P,P'-diisopropyl ester from 3-picolyl chloride ja P,P'-dimethyl P,P'-diisopropyl methylenebisphosphonate.

[2-(4-Pyridinyl)ethylidene]bisphosphonic acid tetraethyl ester from 4-picolyl chloride.

Further, by using as a base litium diisopropylamide, one may prepare

[[(4-Chlorophenyl)thio)methylidene)bisphosphonic acid P,P'-dimethyl P,P'-bis(trimethylsilyl) ester.

[2-(2-Pyridinyl)ethylidene]bisphosphonic acid P-ethyl P,P',P'-tris(trimethylsilyl) ester.

[2-(3-Pyridinyl)ethylidene]bisphosphonic acid P-methyl P,P',P'-tris(trimethylsilyl) ester

[[(4-Chlorophenyl)thio)methylidene)bisphosphonic acid P-ethyl P,P',P'-tris(trimethylsilyl) ester.

Example 1

**Preparation of
[[(6-Methyl-2-pyridinyl)amino]methylidene]bisphosphonic Acid P,P-diethyl Ester**

Into an acetonitrile solution of [[(6-methyl-2-pyridinyl)amino]methylidene]bisphosphonic acid tetraethyl ester (0.02 moles) and sodium iodide (0.04 moles) chlorotrimethylsilane (0.042 moles) was slowly added at room temperature. The solution was stirred for 3 hours, whereafter the solvent was evaporated at reduced pressure. The evaporation residue was dissolved in a small amount of warm water, and the solution was made alkaline with a dilute sodium hydroxide solution. The product was precipiated by adding ethanol (31-P NMR 11.34/22.79 ppm, J=34.3; $D_2O$).

In a corresponding manner the following esters and their sodium salts may be prepared:

[[(2-Pyridinyl)thio]methylidene]bisphosphonic acid P,P-diisopropyl ester from the corresponding tetraisopropyl ester (31-P NMR 9.34/20.44 ppm; J=14.9 Hz; $D_2$).

[[(2-Pyridinyl)thio]methylidene]bisphosphonic acid P,P-diethyl ester from the corresponding tetraethyl ester.

[[(3-Pyridinyl)thio]methylidene]bisphosphonic acid P,P-diisopropyl ester from the corresponding tetraisopropyl ester.

[[(4-Pyridinyl)thio]methylidene]bisphosphonic acid P,P-diethyl ester from the corresponding tetraethyl ester.

[2-(2-Pyridinyl)ethylidene]bisphosphonic acid P',P'-diisopropyl ester from the corresponding P,P-dimethyl P',P'-diisopropyl ester.

[2-(3-Pyridinyl)-1-hydroxyethylidene]bisphosphonic acid P',P'-diethyl ester from the corresponding P,P-dimethyl P',P'-diethyl ester

[[(4-Chlorophenyl)thio]methylidene]bisphosphonic acid P,P-diisopropyl ester from the corresponding tetraisopropyl ester (31-P NMR 10.84/21.38 ppm, J=15.2 Hz; $D_2O$).

[[(6-Methyl-2-pyridinyl)amino]methylidene]bisphosphonic acid P,P-diethyl ester from the corresponding tetraethyl ester (31-P NMR 11.34/22.79 ppm, J=34.3 Hz; $D_2O$).

[[(4-Methyl-2-pyridinyl)amino]methylidene]bisphosphonic acid P,P-diethyl ester from the corresponding tetraethyl ester (31-P NMR 11.43/22.83 ppm, J=35.0 Hz; $D_2O$).

[2-(3-Pyridinyl)ethylidene]bisphosphonic acid P,P-diethyl ester from the corresponding tetraethyl ester.

(3-Pyridinylamino)methylidene]bisphosphonic acid P,P-diethyl ester from the corresponding tetraethyl ester.

Example 2

**Preparation of
[[(4-Chlorophenyl)thio]methylidene)-bisphosphonic Acid Monoisopropyl Ester and its Trisodium Salt**

The tetraisopropyl ester of [[(4-chlorophenyl)thio]methylidene]bisphosphonic acid (0.02 moles) was dissolved in dichloromethane, and to' the solution was slowly added at room temperature bromotrimethylsilane (0.062 moles). The solution was stirred at room temperature for 3 hours, whereafter the solvent was evaporated at reduced pressure.

The evaporation residue was dissolved in a small amount of water and the solution was made alkaline with a dilute sodium hydroxide solution. The product was precipitated by adding ethanol (31-P NMR 12.21/18.25 ppm, J=9.8 Hz; $D_2O$).

Example 3

Preparation of
[[(2-Pyridyl)thio]methylidene]bisphosphonic Acid
Triisopropyl Ester and its Sodium Salt

[[(2-Pyridyl)thio]methylidene]bisphosphonic acid tetraisopropyl ester (0.02 moles) was dissolved in acetonitrile, and to the solution chloro(tert-butyl)(dimethyl)silane (0.022 moles) dissolved in acetonitrile was slowly added. The solution was stirred for 4 hours at 60° C. The solvent was evaporated and the evaporation residue was dissolved in a small amount of water. The solution was made alkaline with a dilute sodium hydroxide solution and the product precipitated by adding ethanol (31-P NMR 7.78/23.76 ppm, J=9.6 Hz; $D_2O$).

In a corresponding manner the following compounds using in the place of chloro(tert-butyl)(dimethyl)silane for example bromotrimethylsilane (1 equivalent) may be prepared:

[2-(2-Pyridinyl)ethylidene]bisphosphonic acid trimethyl ester from the corresponding tetramethyl ester.

[2-(3-Pyridinyl)ethylidene]bisphosphonic acid triethyl ester from the corresponding tetraethyl ester.

[[(3-Pyridinyl)thio]methylidene]bisphosphonic acid triethyl ester from the corresponding tetraethyl ester.

[[(2-Pyridinyl)thio]methylidene]bisphosphonic acid dimethyl isopropyl ester from the corresponding isopropyl trimethyl ester.

[2-(3-pyridinyl)ethylidene]bisphosphonic acid triisopropyl ester (31-P NMR 26.23/15.09 ppm; $CDCl_3$).

[[(4-Methyl-2-pyridinyl)amino]methylidene]bisphosphonic acid triethyl ester from the corresponding tetraethyl ester (31-P NMR 8.62/26.15 ppm, J=25.4 Hz; $D_2O$).

[1-Hydroxy-2-(3-pyridinyl)ethylidene]bisphosphonic acid triisopropyl ester from the corresponding tetraisopropyl ester.

Example 4

Preparation of
[[(3-Methyl-2-pyridinyl)amino]methylidene)
Bisphosphonic Acid P,P'-diethyl Ester

[[(3-methyl-2-pyrdinyl)amino]methylidene) bisphosphonic acid tetraethyl ester (0.015 moles) was dissolved in aqueous ethanol and concentrated sodium hydroxide solution (0.05 moles) was added to the solution. The solution was stirred over night. The solvent was evaporated and the evaporation residue stirred into ethanol. The product was filtered and dried (31-P NMR 16.60 ppm; $D_2O$).

In a corresponding manner may be prepared:

[[(2-Pyridinyl)amino]methylidene]bisphosphonic acid P,P'-diethyl ester (31-P NMR 16.37 ppm; $D_2O$).

[[(4-Pyridinyl)amino]methylidene]bisphosphonic acid P,P'-diethyl ester.

[[(4-chlorophenyl)thio]methylidene]bisphosphonic acid P,P'-diisopropyl ester from the corresponding tetraisopropyl ester (3]-P NMR 14.00 ppm; $D_2O$).

[2-(2-Pyridinyl)ethylidene]bisphosphonic acid P,P'-diisopropyl ester from the corresponding tetraisopropyl ester.

[2-(3-Pyridinyl)ethylidene]bisphosphonic acid P,P'-diethyl ester from the corresponding tetraethyl ester.

[1-Hydroxy-2-(2-pyridinyl)ethylidene]bisphosphonic acid P,P'-dimethyl ester from the corresponding tetramethyl ester.

[1-Hydroxy-2-(3-pyridinyl)ethylidene]bisphosphonic acid P,P'-diethyl ester from the corresponding tetraethyl ester.

[[(2-Hydroxy-3-pyridinyl)amino]methylidene]bisphosphonic acid P,P'-diethyl ester from the corresponding tetraethyl ester.

[[(2-Methoxy-3-pyridinyl)amino]methylidene]bisphosphonic acid P,P'-diethyl ester from the corresponding tetraethyl ester.

[[(4,6-Dihydroxy-2-pyrimidyl)amino]methylidene]bisphosphonic acid P,P'-diethyl ester from the corresponding tetraethyl ester.

Example 5

Preparation of
[[(6-Methyl-2-pyridinyl)amino]methylidene)bisphosphonic Acid P,P'-diethyl Ester and its Disodium Salt The tetraethyl ester of [[(6-methyl-2-pyridinyl)amino]methylidene)bisphosphonic acid (0.009 moles) was dissolved in a mixture of morpholine (40 ml) and dichloromethane (50 ml). The solution was stirred for a day. The solvent was evaporated and the morpholinium salt of the product was dissolved in acetone. To the solution a sodium hydroxide solution was added (0.02 moles), whereby the product precipitated in the form of the disodium salt (31-P NMR 16.45 ppm; $D_2O$).

In the same manner may be prepared, also using instead of morpholine e.g. piperidine, 2-methylpiperidine or 4-benzylpiperazine

[[(4-pyridinyl)amino]methylidene]bisphosphonic acid P,P'-dimethyl ester,

[[(3-pyridinyl)thio]methylidene]bisphosphonic acid P,P'-diethyl ester,.

[[(3-pyridinyl)amino]methylidene]bisphosphonic acid P,P'-dimethyl ester,

[2-(2-pyridinyl)ethylidene]bisphosphonic acid P,P'-dimethyl ester.

Example 6

Preparation of
[[(4-Methyl-2-pyridinyl)amino]methylidene)bisphosphonic Acid P,P'-diethyl Ester and its Disodium Salt The tetraethyl ester of [[(4-methyl-2-pyridinyl)amino]methylidene)bisphosphonic acid (0.02 moles) was dissolved in dichloromethane and to the solution bromotrimethylsilane (0.042 moles) was slowly added at room temperature. The solution was stirred for 3 hours. The solvent was evaporated at reduced pressure. To the evaporation residue, a sodium hydroxide solution (0.04 moles) was added as well as an equal volume of ethanol, whereby the product precipitated as the disodium salt (31-P NMR 16.39 ppm; $D_2O$).

In a corresponding manner may be prepared:

[2-(2-Pyridinyl)ethylidene]bisphosphonic acid P,P'-diisopropyl ester from the corresponding tetraisopropyl ester.

[[(4-Chlorophenyl)thio]methylidene)bisphosphonic acid P,P'-dimethyl ester from the corresponding tetramethyl ester.

[[(2-Pyridinyl)thio]methylidene]bisphosphonic acid P,P'-dimethyl ester from the corresponding tetramethyl ester.

[2-(2-Pyridinyl)ethylidene]bisphosphonic acid P,P'-diisopropyl ester from the corresponding P,P'-dimethyl P,P'-diisopropyl ester.

[[(3-Pyridinyl)thio]methylidene]bisphosphonic acid P,P'-dimethyl ester from the corresponding tetramethyl ester.

[2-(3-Pyridinyl)ethylidene]bisphosphonic acid P,P'-diisopropyl ester from the corresponding P,P'-dimethyl P,P'-diisopropyl ester.

[1-Hydroxy-2-(3-pyridinyl)ethylidene]bisphosphonic acid P,P'-diisopropyl ester from the corresponding tetraisopropyl ester.

Example 7

Preparation of [[(6-Methyl-2-pyridinyl)amino]methylidene)bisphosphonic Acid Monoethyl Ester and its Trisodium Salt

[[(6-methyl-2-pyridinyl)amino]methylidene)bisphosphonic acid P,P'-diethyl ester prepared according to the Example 4 (0.01 moles) was slurried in a 15% hydrochloric acid solution and the solution was stirred at 80° C. The progress of the reaction was followed with $^{31}P$ NMR. After the reaction had ceased the mixture was evaporated to dryness, the evaporation residue dissolved in a sodium hydroxide solution and the trisodium salt formed precipitated by adding ethanol. The product was filtered and dried (yield 60%, 31-P NMR 11.73/19.11 ppm; J=24.7 Hz; D₂O).

In a corresponding manner may be prepared:
[1-Hydroxy-2-(2-pyridinyl)ethylidene]bisphosphonic acid monoisopropyl ester from the corresponding P,P'-diisopropyl ester.
[2-(3-pyridinyl)ethylidene]bisphosphonic acid monoisopropyl ester (31-P NMR 18.76/17.45 ppm; CDCl₃).
[[(2-Pyridinyl)thio]methylidene]bisphosphonic acid monoisopropyl ester from the corresponding P,P'-diisopropyl ester (31-P NMR 11.79/18.05 ppm, J=9.6 Hz; D₂O).
[1-Hydroxy-2-(3-pyridinyl)ethylidene]bisphosphonic acid monoisopropyl ester from the corresponding P,P'-diisopropyl ester.
[[(3-Pyridinyl)thio]methylidene]bisphosphonic acid monoisopropyl ester from the corresponding P,P'-diisopropyl ester (31-P NMR 11.79/18.05 ppm, J=9.6 Hz; D₂O).
[[(4-Methyl-2-pyridinyl)amino]methylidene]bisphosphonic acid monomethyl ester.
[[(3-Methyl-2-pyridinyl)amino]methylidene]bisphosphonic acid monomethyl ester.
[2-(2-Pyridinyl)ethylidene]bisphosphonic acid monoisopropyl ester.

Example 8

Preparation of [[(2-Pyridyl)thio]methylidene]bisphosphonic Acid P,P'-diisopropyl Ester

[[(2-pyridyl)thio]methylidene]bisphosphonic acid tetraisopropyl ester (0.01 moles) was dissolved in acetone, and to the solution sodium iodide (0.023 moles) was added. The solution was stirred at room temperature for 8 hours, whereafter it was filtered. The solvent was evaporated. The product was isolated from the evaporation residue as the disodium salt in a manner described in the previous examples (yield 59%, 31-P NMR 14.09 ppm; D₂O).

In the corresponding manner may be prepared:
[[(2-Pyridyl)amino]methylidene]bisphosphonic acid P,P'-dimethyl ester from the corresponding tetramethyl ester (31-P NMR).

[[2-(3-Pyridinyl)thio]methylidene]bisphosphonic acid P,P'-diisopropyl ester from the corresponding tetraisopropyl ester.
[1-Hydroxy-2-(3-pyridinyl)ethylidene]bisphosphonic acid P,P'-diethyl ester from the corresponding tetraethyl ester.
[[2-(4-Pyridinyl)thio]methylidene]bisphosphonic acid P,P'-diisopropyl ester from the corresponding tetraisopropyl ester.
[1-Hydroxy-2-(2-pyridinyl)ethylidene]bisphosphonic acid P,P'-diethyl ester from the corresponding tetraethyl ester.

Example 9

Preparation of [Hydroxy-2-(3-pyridinyl)ethylidene]bisphosphonic Acid Monomethyl Ester Finely ground [1-hydroxy-2-(3-pyridinyl)ethylidene]-bisphosphonic acid (0.005 moles) was slurried into 100 ml of chloroform and to the mixture 25 ml of an appr. 2% ether solution of diazomethane was added at room temperature. After the addition, mixing was continued for 1 hour. The mixture was evaporated under reduced pressure (yield 38%).

Example 10

Preparation of [[(2-Pyridinyl)thio]methylidene]bisphosphonic Acid Monoisopropyl Ester and its Trisodium Salt

[[(2-pyridinyl)thio]methylidene]bisphosphonic acid tetraisopropyl ester (0.01 moles) was dissolved in toluene and to the solution methane sulphonic acid (0.06 moles) was added. The solution was stirred while heating and the progress of hydrolysis was followed with 31-P NMR. The mixture was cooled and the solvent evaporated under reduced pressure. The evaporation residue was dissolved in a dilute sodium hydroxide solution and the product was precipitated by adding acetone (yield 62%, 31-P NMR 11.79/18.05 ppm, J=9.6 Hz; D₂O).

In the same manner may be prepared:
[2-(3-Pyridinyl)-1-hydroxyethylidene]bisphosphonic acid P,P'-diisopropyl ester from the corresponding tetraisopropyl ester.
[2-(3-Pyridinyl)-t-hydroxyethylidene]bisphosphonic acid monomethyl ester from the corresponding tetramethyl ester.
[2-(2-Pyridinyl)-1-hydroxyethylidene]bisphosphonic acid P,P'-diisopropyl ester from the corresponding tetraisopropyl ester.
[2-(3-Pyridinyl)ethylidene]bisphosphonic acid P,P-diisopropyl ester from the corresponding tetraisopropyl ester.

Example 11

Preparation of [[(4-Chlorophenyl)thio]methylidene]bisphosphonic Acid P,P'-dimethyl Ester and its Disodium Salt A mixture of [[(4-chlorophenyl)thio]methylidene]bisphosphonic acid P,P'-dimethyl P,P'-bis(trimethylsilyl) ester (0.01 moles) and dilute hydrochloric acid was stirred at 0° C. for 0.5 hours. To' the filtered solution' dilute sodium hydroxide was added (0.01 moles excess) and the product precipitated with ethanol.

In a corresponding manner may be prepared

[2-(2-Pyridinyl)ethylidene]bisphosphonic acid monoethyl ester

[2-(3-Pyridinyl)ethylidene]bisphosphonic acid monomethyl ester

[[(4-chlorophenyl)thio]methylidene]bisphosphonic acid monoethyl ester.

We claim:

1. Bisphosphonic acid derivatives having the formula I

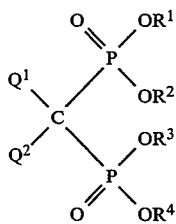

in which formula $R^1$, $R^2$, $R^3$ and $R^4$ independently are a straight or branched, optionally unsaturated $C_1$-$C_7$-alkyl or $C_2$-$C_7$-alkenyl or hydrogen, whereby in the formula I at least one of the groups $R^1$, $R^2$, $R^3$ and $R^4$ is hydrogen and at least one of the groups $R^1$, $R^2$, $R^3$ and $R^4$ is different from hydrogen, $Q^1$ is hydrogen or hydroxyl, $Q^2$ is the group

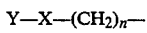

Y—X—(CH$_2$)$_n$— wherein Y is phenyl, pyridinyl, piperidinyl or pyrimidinyl which is unsubstituted or substituted by $C_1$-$C_4$-alkyl, $C_1$-$C_4$-alkoxy, halogen, hydroalkyl or nitro, X is S or NH, and n=0, or X is a direct bond and n=1, provided that as a ring atom of the ring Y and/or a chain atom of the group X, there is always at least one heteroatom from the group of N and S, including the stereoisomers, or a pharmacologically acceptable salt thereof.

2. Mono- or dimethyl, mono- or diethyl, mono- or diisopropyl esters of the formula I according to the claim 1, wherein $Q^1$ is hydrogen and Y is unsubstituted or methyl-substituted pyridine or piperidine, n is 0 and X is NH, or S.

3. Compound of the formula I according to the claim 1, which is

[[(6-methyl-2-pyridinyl)amino]methylidene]bisphosphonic acid P,P'-diethyl ester,

[[(2-pyridinyl)amino]methylidene]bisphosphonic acid P,P'-diethyl ester,

[[(2-pyridinyl)amino]methylidene]bisphosphonic acid P,P-dimethyl ester,

[[(3-methyl-2-pyridinyl)amino]methylidene]bisphosphonic acid P,P'-diethyl ester,

[[(4-methyl-2-pyridinyl)amino]methylidene]bisphosphonic acid P,P'-diethyl ester,

[[(2-pyridinyl)thio]methylidene]bisphosphonic acid monoisopropyl ester,

[[(4-chlorophenyl)thio]methylidene]bisphosphonic acid P,P'-dimethyl and monoetyl ester,

[[(6-methyl-2-pyridinyl)amino]methylidene]bisphosphonic acid monoethyl ester,

[[(3-methyl-2-pyridinyl)amino]methylidene]bisphosphonic acid monomethyl ester,

[[1-hydroxy-2-(3-pyridinyl)]ethylidene]bisphosphonic acid monoisopropyl ester,

[[1-hydroxy-2-(3-pyridinyl)]ethylidene]bisphosphonic acid monomethyl ester,

[2-(2-pyridinyl)ethylidene]bisphosphonic acid monoisopropyl ester,

[2-(3-pyridinyl)ethylidene]bisphosphonic acid monomethyl ester,

[[(3-pyridinyl)amino]methylidene]bisphosphonic acid P,P'-dimethyl ester,

[[(3-pyridinyl)thio]methylidene]bisphosphonic acid P,P'-diethyl ester,

[[(4-pyridinyl)thio]methylidene]bisphosphonic acid P,P'-diethyl ester,

[[(3-pyridinyl)thio]methylidene]bisphosphonic acid monoisopropyl ester.

4. Pharmaceutical composition for the treatment of disorders relating to the metabolism of calcium and other bivalent metals and the pyrophosphate functions of the body, characterized in that it contains as the active agent a compound having the formula I according to claim 1.

5. A method of treating a physiological disorder by administering to a patient a pharmacological composition for the treatment of disorders relating to the metabolism of calcium and other bivalent metals and the pyrophosphate functions of the body, characterized in that it has as an active agent a compound having the formula I according to claim 1.

* * * * *